US008070693B2

(12) United States Patent
Ayala et al.

(10) Patent No.: US 8,070,693 B2
(45) Date of Patent: Dec. 6, 2011

(54) ARTICULATING STEERABLE WIRE GUIDE

(75) Inventors: Juan Carlos Ayala, Santiago (CL);
Matthew P. Carter, Dobson, NC (US);
David M. Hardin, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 1203 days.

(21) Appl. No.: 11/599,522

(22) Filed: Nov. 14, 2006

(65) Prior Publication Data
US 2007/0123804 A1 May 31, 2007

Related U.S. Application Data

(63) Continuation-in-part of application No. 11/234,990, filed on Sep. 26, 2005.

(60) Provisional application No. 60/738,760, filed on Nov. 21, 2005, provisional application No. 60/614,908, filed on Sep. 30, 2004.

(51) Int. Cl.
*A61B 5/00* (2006.01)
(52) U.S. Cl. ........................................ 600/585
(58) Field of Classification Search ........... 600/433, 600/434, 585; 604/164.13
See application file for complete search history.

(56) References Cited

U.S. PATENT DOCUMENTS

| 892,472 A | 7/1908 | Walker |
| 3,791,387 A | 2/1974 | Itoh |
| 3,890,977 A | 6/1975 | Wilson ........................ 128/418 |
| 4,176,662 A | 12/1979 | Frazer |
| 4,207,872 A | 6/1980 | Meiri et al. |
| 4,281,660 A | 8/1981 | Fujiwara ........................ 600/375 |
| 4,310,789 A | 1/1982 | Mank et al. .................... 318/587 |
| 4,326,530 A | 4/1982 | Fleury, Jr. ........................ 606/47 |
| 4,447,227 A | 5/1984 | Kotsanis |
| 4,545,390 A | 10/1985 | Leary ............................ 600/462 |
| 4,800,890 A | 1/1989 | Cramer ......................... 600/434 |

(Continued)

FOREIGN PATENT DOCUMENTS

EP   0 667 115 A1   1/1995

(Continued)

OTHER PUBLICATIONS

Canadian Office Action dated Nov. 23, 2009 from corresponding Canadian Patent Application 2,625,053 (3p).

(Continued)

*Primary Examiner* — Max Hindenburg
*Assistant Examiner* — Jonathan M Foreman
(74) *Attorney, Agent, or Firm* — Brinks Hofer Gilson & Lione

(57) ABSTRACT

A steerable wire guide comprises first and second members interconnected to form a unitary composite structure. The members slide relative to each other such that the leading portion of the composite structure bends in a first or second direction. The composite structure comprises a soft body portion at its distal end and a rigid body portion at its proximal end. Various cross-sections are disclosed. In an alternate embodiment, the wire guide comprises a first guiding wire section, a wire loop section and a second guiding wire section, the wire component being folded back on itself to form a generally central wire loop section; and a tubular sheath surrounding the first guiding wire section and the second guiding wire section. The first and second members or guiding wire sections can be connected to a removable handle to facilitate control and maneuverability of the wire guide.

5 Claims, 9 Drawing Sheets

U.S. PATENT DOCUMENTS

| | | | |
|---|---|---|---|
| 5,037,391 A | 8/1991 | Hammerslag et al. | 604/528 |
| 5,054,501 A | 10/1991 | Chuttani et al. | 600/585 |
| 5,069,217 A | 12/1991 | Fleischhacker, Jr. | 600/585 |
| 5,078,716 A | 1/1992 | Doll | |
| 5,114,402 A | 5/1992 | McCoy | 604/95 |
| 5,211,636 A | 5/1993 | Mische | 604/264 |
| 5,221,270 A | 6/1993 | Parker | 604/282 |
| 5,300,048 A | 4/1994 | Drewes, Jr. et al. | 604/280 |
| 5,334,168 A | 8/1994 | Hemmer | 604/531 |
| 5,337,732 A | 8/1994 | Grundfest et al. | |
| 5,345,925 A | 9/1994 | Alfred, III et al. | |
| 5,349,964 A | 9/1994 | Imran et al. | 600/585 |
| 5,358,479 A | 10/1994 | Wilson | 604/95 |
| 5,376,083 A | 12/1994 | Mische | 604/264 |
| 5,387,219 A | 2/1995 | Rappe | 606/108 |
| 5,398,670 A | 3/1995 | Ortiz et al. | |
| 5,433,200 A | 7/1995 | Fleischhacker, Jr. | 600/434 |
| 5,490,845 A | 2/1996 | Racz | 604/266 |
| 5,498,249 A | 3/1996 | Quinn | 604/528 |
| 5,522,819 A | 6/1996 | Graves et al. | |
| 5,531,685 A | 7/1996 | Hemmer et al. | 604/95.05 |
| 5,595,565 A | 1/1997 | Treat et al. | |
| 5,604,531 A | 2/1997 | Iddan et al. | |
| 5,613,973 A | 3/1997 | Jackson et al. | 606/113 |
| 5,643,281 A | 7/1997 | Suhocki et al. | 606/133 |
| 5,728,122 A | 3/1998 | Leschinsky et al. | 606/213 |
| 5,730,704 A | 3/1998 | Avitall | 600/374 |
| 5,824,031 A | 10/1998 | Cookston et al. | 607/122 |
| 5,836,947 A | 11/1998 | Fleischmann et al. | |
| 5,879,295 A | 3/1999 | Li et al. | 600/373 |
| 5,885,383 A | 3/1999 | Mitose et al. | 148/564 |
| 5,885,741 A | 3/1999 | Akamastu et al. | 430/106.6 |
| 5,904,648 A | 5/1999 | Arndt et al. | 600/120 |
| 6,007,482 A | 12/1999 | Madni et al. | |
| 6,056,743 A | 5/2000 | Ellis et al. | 606/15 |
| 6,102,918 A | 8/2000 | Kerr | 606/108 |
| 6,162,171 A | 12/2000 | Ng et al. | |
| 6,190,382 B1 | 2/2001 | Ormsby et al. | |
| 6,203,525 B1 | 3/2001 | Whayne et al. | |
| 6,277,139 B1 | 8/2001 | Levinson et al. | 606/200 |
| 6,299,612 B1 | 10/2001 | Ouchi | 606/47 |
| 6,371,970 B1 | 4/2002 | Khosravi et al. | 606/200 |
| 6,379,319 B1 | 4/2002 | Garibotto et al. | 600/585 |
| 6,425,895 B1 | 7/2002 | Swanson et al. | 606/41 |
| 6,454,758 B1 | 9/2002 | Thompson et al. | 604/528 |
| 6,464,699 B1 | 10/2002 | Swanson | 606/41 |
| 6,500,167 B1 | 12/2002 | Webster, Jr. | 604/528 |
| 6,530,913 B1 | 3/2003 | Giba et al. | 604/528 |
| 6,551,302 B1 | 4/2003 | Rosinko et al. | 604/525 |
| 6,591,144 B2 | 7/2003 | Pigott | 607/119 |
| 6,592,581 B2 | 7/2003 | Bowe | 606/41 |
| 6,620,179 B2 | 9/2003 | Boock et al. | 606/159 |
| 6,720,402 B2 | 4/2004 | Langer et al. | 528/76 |
| 6,730,058 B2 | 5/2004 | Hayzelden | 604/95.04 |
| 2002/0010426 A1 | 1/2002 | Clayman et al. | 604/170.01 |
| 2002/0016604 A1 | 2/2002 | Boock et al. | 606/159 |
| 2002/0032455 A1 | 3/2002 | Boock et al. | |
| 2003/0181827 A1* | 9/2003 | Hojeibane et al. | 600/585 |
| 2004/0016849 A1 | 1/2004 | Jakubowski et al. | 244/137.4 |
| 2004/0030259 A1 | 2/2004 | Dae et al. | |
| 2004/0082881 A1 | 4/2004 | Grewe et al. | 600/585 |
| 2004/0106897 A1 | 6/2004 | Thompson et al. | 604/95.04 |
| 2004/0111020 A1 | 6/2004 | Long | |
| 2004/0125139 A1 | 7/2004 | Beck et al. | 345/764 |
| 2004/0193032 A1 | 9/2004 | Mogul | 600/374 |
| 2004/0193205 A1 | 9/2004 | Burgermeister | 606/194 |
| 2004/0199087 A1 | 10/2004 | Swain et al. | |
| 2004/0199088 A1* | 10/2004 | Bakos et al. | 600/585 |
| 2004/0215208 A1 | 10/2004 | Foushee et al. | 606/108 |
| 2005/0027243 A1 | 2/2005 | Gibson et al. | 604/95.04 |
| 2005/0038412 A1 | 2/2005 | Rabiner et al. | 604/528 |
| 2005/0043779 A1 | 2/2005 | Wilson | 623/1.11 |
| 2005/0080356 A1 | 4/2005 | Dapolito et al. | 600/585 |
| 2005/0096567 A1* | 5/2005 | Reynolds et al. | 600/585 |
| 2005/0096590 A1 | 5/2005 | Gullickson et al. | 604/95.04 |
| 2005/0107737 A1* | 5/2005 | McDaniel | 604/95.04 |
| 2005/0261663 A1 | 11/2005 | Patterson et al. | |
| 2006/0100544 A1 | 5/2006 | Ayala et al. | 600/585 |
| 2007/0060997 A1 | 3/2007 | De Boer | |
| 2007/0083253 A1 | 4/2007 | Fischell et al. | |

FOREIGN PATENT DOCUMENTS

| | | |
|---|---|---|
| EP | 0 827 712 A2 | 11/1999 |
| EP | 1 346 747 A | 9/2003 |
| EP | 1 532 999 A2 | 11/2004 |
| JP | 07088191 | 4/1995 |
| WO | WO 94/05200 | 3/1994 |
| WO | WO 97/31677 | 9/1997 |
| WO | WO 98/11896 | 3/1998 |
| WO | WO 98/19608 | 5/1998 |
| WO | WO 99/30610 | 6/1999 |
| WO | WO 99/34726 | 7/1999 |
| WO | WO 99/53827 | 10/1999 |
| WO | WO 00/22975 | 4/2000 |
| WO | WO 00/44275 | 8/2000 |
| WO | WO 01/08548 A1 | 2/2001 |
| WO | WO 01/67967 A1 | 9/2001 |
| WO | WO 2004/050161 A | 6/2004 |
| WO | WO 2004/089456 A | 10/2004 |
| WO | WO 2006/639216 A2 | 4/2006 |

OTHER PUBLICATIONS

Hodgson et al., *Shape memory alloys*, [online], [retrieved on Dec. 9, 2005]. Retrieved from Johnson Matthey database using Internet <URL: http://www.jmmedical.com/html/_shape_memory_alloys_.html>.

Lin, *Shape memory alloys and Their Application* (1996, 1998), [online], [retrieved Dec. 5, 2005]. Retrieved from Stanford University database using Internet <URL: http://www.stanford.edu/~richlin/sma/sma.html>.

*Shape memory alloys* (2001), [online], [retrieved on Dec. 9, 2005]. Retrieved from University of Alberta database using Internet <URL: http://www.cs.ualberta.ca/~database/MEMS/sma_mems/sma.html>.

*Two-Way Memory*, [online], [retrieved on Dec. 9, 2005]. Retrieved from Johnson Matthey database using Internet <URL: http://www.jmmedical.com/html/2_way_memory.html>.

Search Report and Annex, mailed Jun. 25, 2007, for PCT Patent Application PCT/US2006/044243, filed Nov. 14, 2006, listing results of PCT search.

Written Opinion, mailed Jun. 25, 2007, for PCT Patent Application PCT/US2006/044243, filed Nov. 14, 2006, giving the PCT Examiner's opinion regarding patentability of the PCT claims.

Long, Gary, Ph.D., et al.; "The Cath-Cam: a new concept in colonoscopy;" Gastrointestinal Endoscopy, vol. 64, No. 6, Dec. 2006, pp. 997-1001.

Mosse, C.A., Ph.D., et al., "Technical Advances and Experimental Devices for Enteroscopy;" Gastrointest Endosc Clin N Am., vol. 9, No. 1, Jan. 1999, pp. 145-161.

International Search Report mailed Jan. 27, 2006 (Annex to Form PCT/ISA/2006) for PCT International Patent Application PCT/US2005/034280.

* cited by examiner

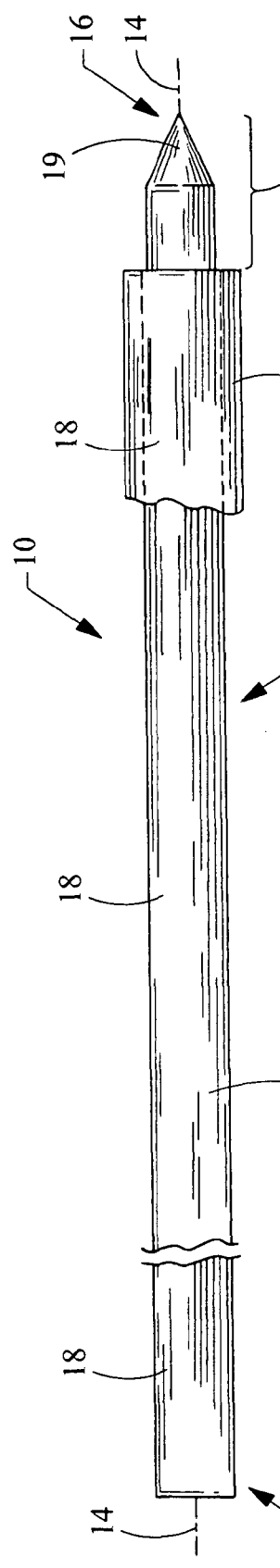

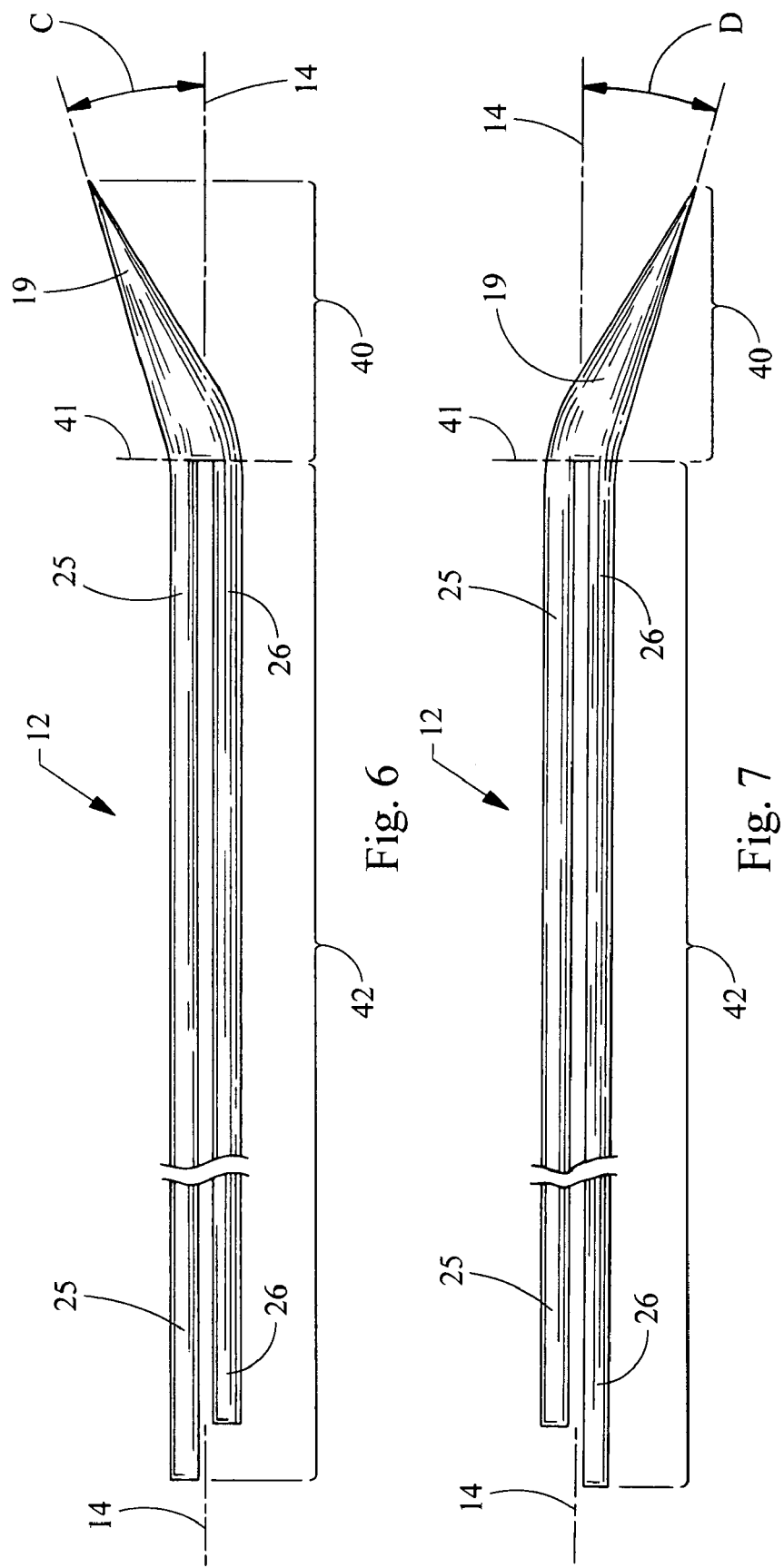

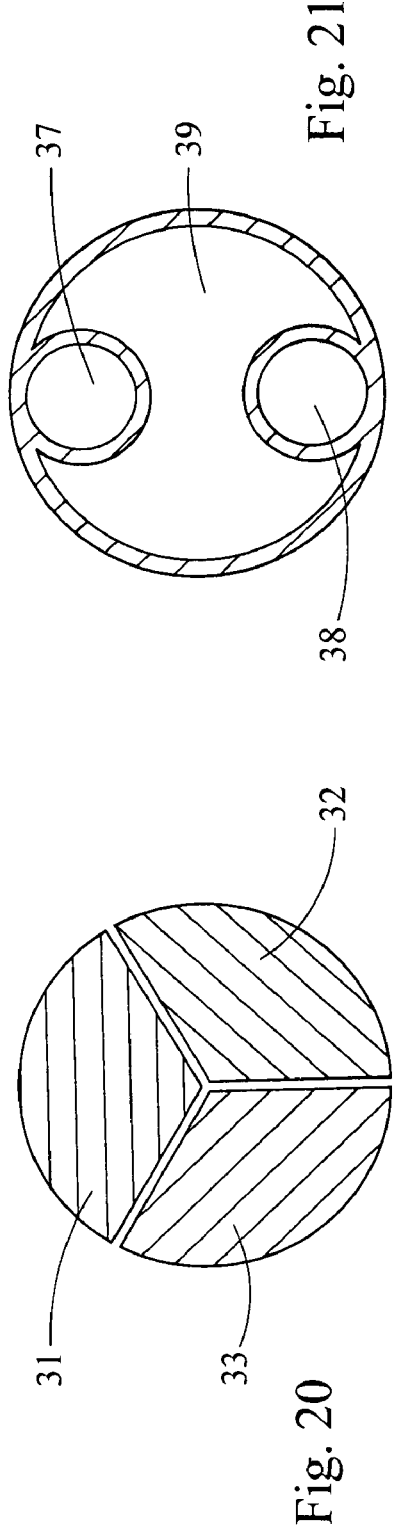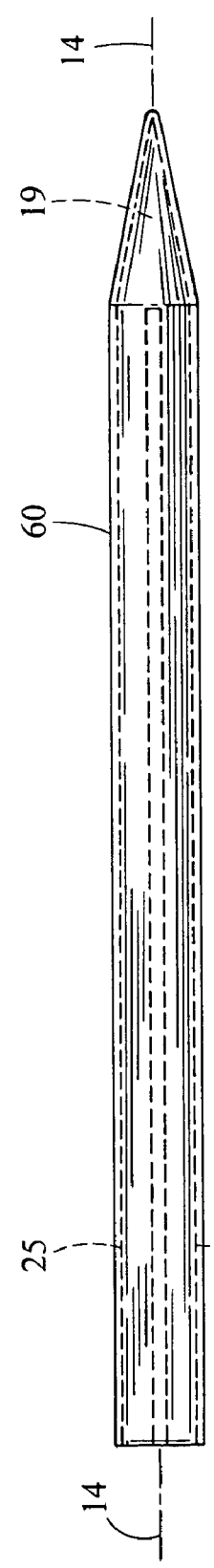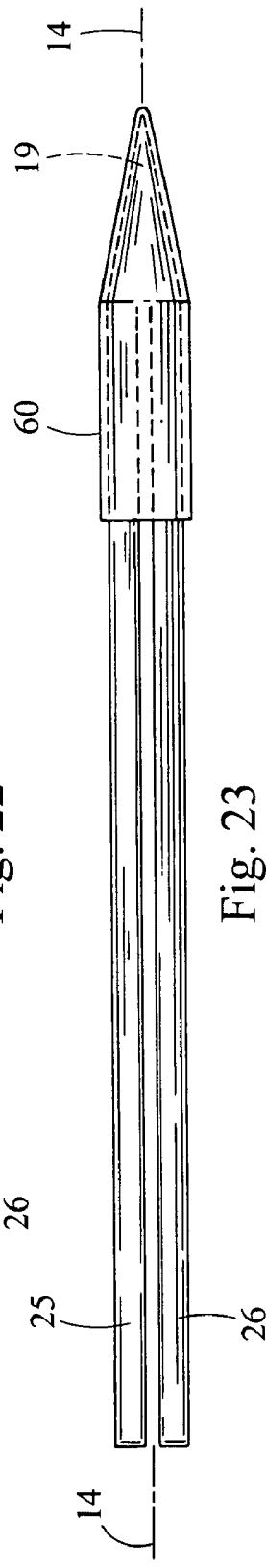
Fig. 20
Fig. 21
Fig. 22
Fig. 23

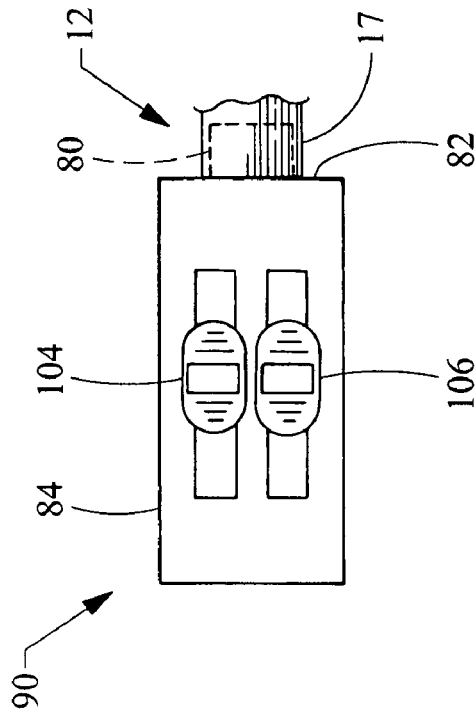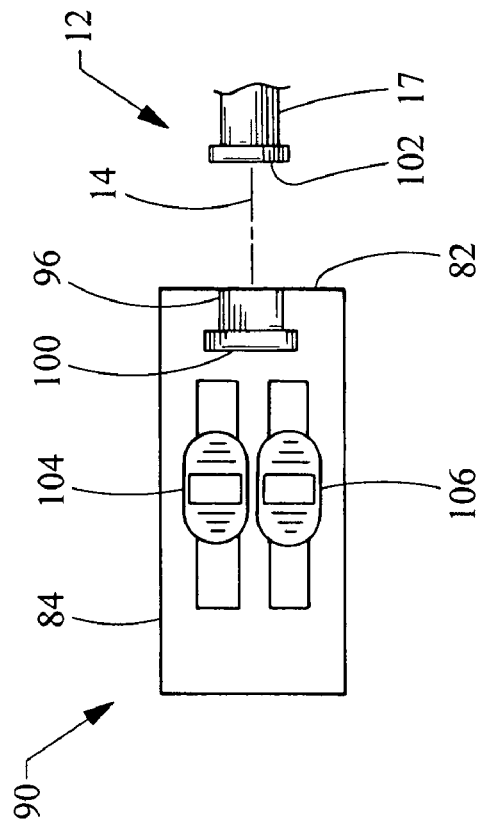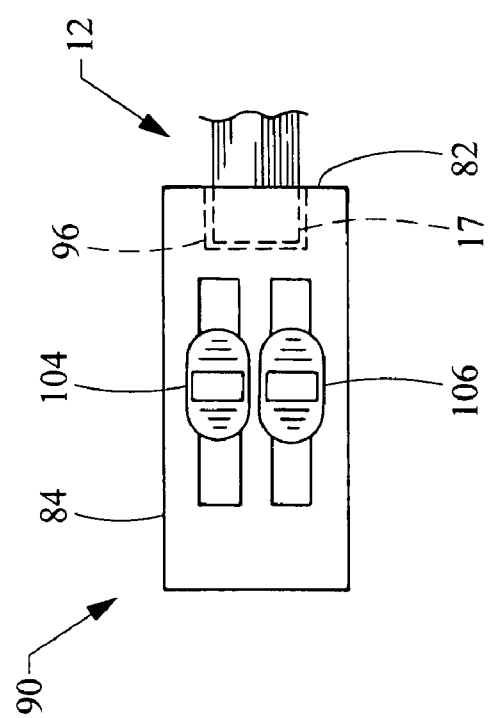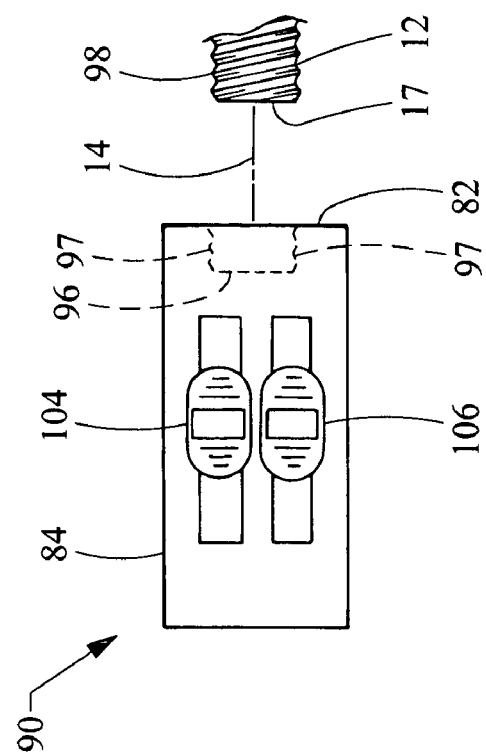

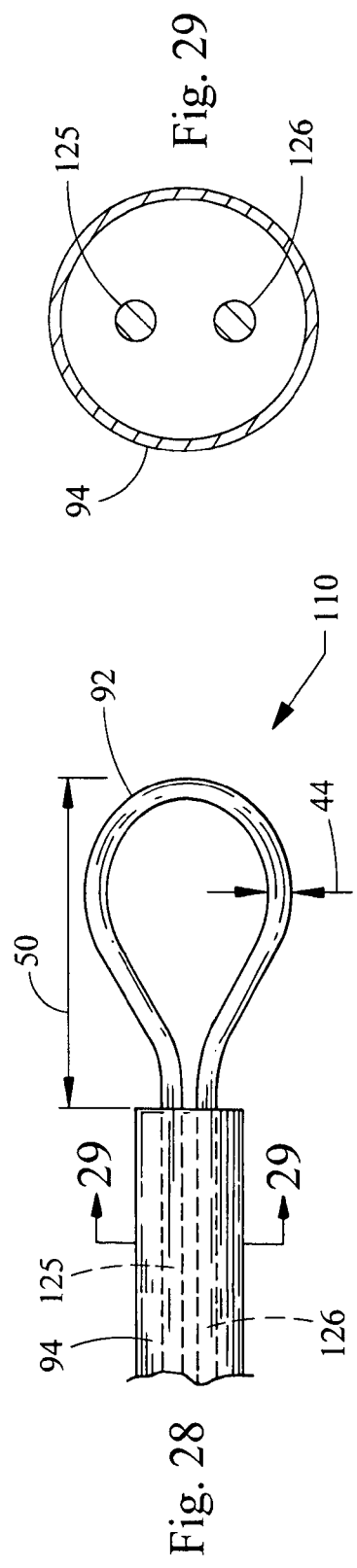
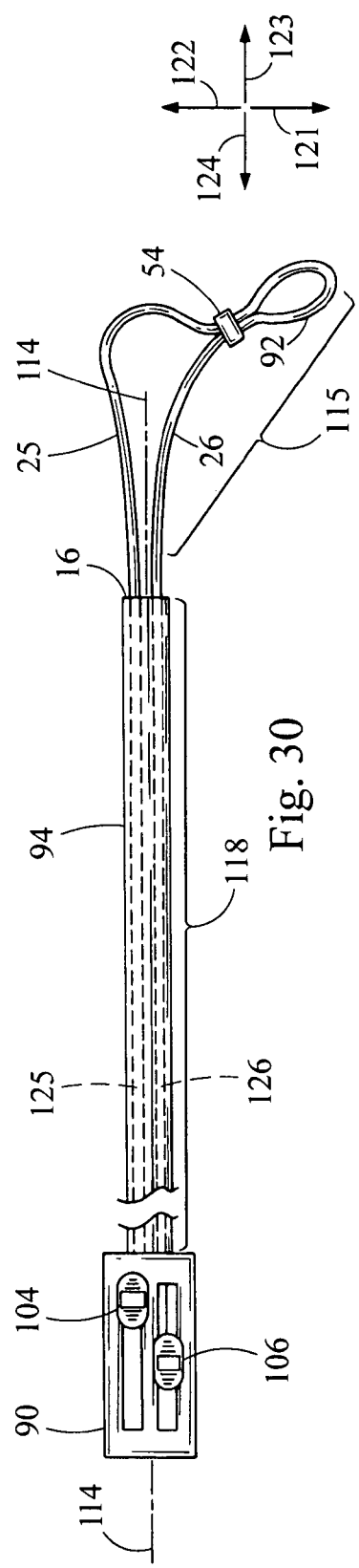
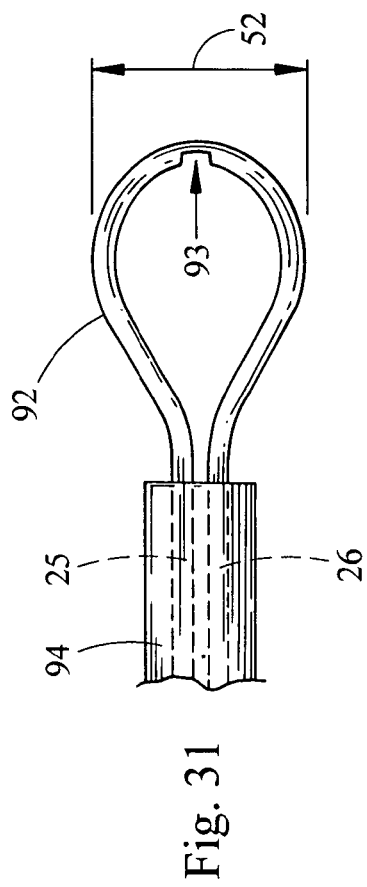
Fig. 28
Fig. 29
Fig. 30
Fig. 31

ARTICULATING STEERABLE WIRE GUIDE

RELATED APPLICATIONS

The priority is claimed of U.S. Provisional Application Ser. No. 60/738,760, filed Nov. 21, 2005, which is a continuation-in-part of Non-Provisional application Ser. No. 11/234,990, filed Sep. 26, 2005, which claims priority to U.S. Provisional Application Ser. No. 60/614,908, filed on Sep. 30, 2004, all of which are incorporated herein by reference.

BACKGROUND

1. Field of Invention

This invention relates generally to devices for use in medical procedures, and more particularly, relates to steerable wire guides used separately or in conjunction with catheters or endoscopes. Specifically, this invention relates to an improved steerable wire guide including interlocking movable component access to hard to reach internal anatomy of a patient.

2. Related Technology

Wire guides are used in various medical procedures involving the gastrointestinal system, including the pancreatobiliary system (i.e., the biliary tree), the stomach, and the esophagus. Wire guides can be long, slender, relatively flexible wires used to access a patient's narrow passageway during minimally invasive medical procedures. Wire guides can be cumbersome as well as requiring constant, delicate manipulation by the treating physician because of the length of the wire guide.

Alternately, wire guides can also be described as elongated flexible members used to provide a path along which another medical device can be moved. The path provided by the wire guide can be used to navigate an alternate medical device, such as a catheter, through a body vessel. In this configuration, the wire guide can provide an established path for inserting other devices, eliminating the need for performing delicate navigation procedures for each device passed through the vessel. The use of wire guides to define such a path is known in the art.

Wire guides must have the ability to be maintained in a stationary position during various medical procedures. In operation, the wire guide is navigated through a body vessel to the desired target location. Once positioned within the body vessel, a second medical device, frequently a cannula such as a catheter can be placed over the wire guide and transported to the desired target location for treatment.

The operator of the wire guide must navigate the wire guide through the body vessel. Often, the body vessel forms a torturous path as a result of natural bends or curves in the body vessel or in the alternative, unnatural impediments, such as tumors or build-ups, which may also exist. The existence of this torturous path makes the navigation of the wire guide difficult. For example, the presence of an impediment may block the wire guide from navigating further into the vessel to reach the target or repair location.

As a result of the complexity of the above-described procedures, physicians often need the assistance of another person to secure the wire guide in addition to any additional medical devices used. Consequently, the physician's assistant must divert his or her attention from his or her primary responsibilities such as checking the patient's vital signs, checking monitors for relevant information and carrying out other tasks to assisting with maintaining the stability of the steerable wire guide.

The related art includes several examples of wire guides having a straight flexible tip and an elongated body portion intended to aid in the navigation of the wire guide. The presence of the straight flexible tip, however, may in fact make navigation more difficult. For example, upon encountering an impediment, the straight flexible tip may bend toward one of the vessel walls. Further, the straight flexible tip may bend and turn back upon itself upon encountering the impediment. As a consequence the straight flexible tip may encounter a sudden sharp turn which makes further navigation difficult.

Examples of successful devices that have been developed to address this need in the art are disclosed in U.S. application Ser. No. 10/719,764, filed Nov. 21, 2003, and entitled "Loop Tip Wire Guide," now U.S. Pat. No. 7,520,881, which claims priority to U.S. Provisional Application Ser. No. 60/430,466, filed on Dec. 2, 2002; and in U.S. application Ser. No. 11/234,990, filed Sep. 26, 2005, and entitled "Steerable Loop Tip Wire Guide," which claims priority to U.S. Provisional Application Ser. No. 60/614,908 filed on Sep. 30, 2004, all of which are incorporated herein by reference.

In the first application, a resilient loop and a closure member are affixed to the distal end of a wire guide. When this device is navigated through a body vessel and encounters an impediment, the distal end of the wire guide does not move relative to the remainder of the wire guide due to the presence of the loop and closure member. Instead, the loop deforms in response to the impediment. The resiliency of the loop creates a force opposing the impediment and directs the loop away from the impediment. Therefore, the remainder of the wire guide following the path created by the loop tip enables the wire guide to navigate around the impediment and continues along the interior of the vessel.

In the latter mentioned application, a steerable wire guide is provided that can be formed with or without a loop. The wire guide further includes a closure member to close the loop. In this configuration, the loop is static and makes a soft loop instead of a pointed end. The wire guide can be easily manipulated once inside the body vessel cavity. The wire guide deforms in accordance with the internal path of the body vessel. Yet, additional improved embodiments of wire guides are desirable.

The general purpose of the present invention overcomes problems in the prior art by providing an improved articulating steerable wire guide having multiple configurations yet sufficiently steerable to provide greater control by the user and safety when deployed. In situations where the point of treatment may be located in a side branch or beyond the bifurcation of the main vessel, there is a need for a wire guide that can be shifted and, durable as to be easily manipulated through the tortuous path. For this reason, a wire guide would be desirable to provide the user with greater ability of control. It would also be desirable to provide a steerable wire guide that can be turned in various degrees and configurations to provide access to any structure without substitution of any of its components.

BRIEF SUMMARY

These and other objects and advantages of this invention will become apparent to a person of ordinary skill in this art upon careful reading of the detailed description of this application including the drawings as presented herein. The present invention relates to an articulating steerable wire guide. In one embodiment, the wire guide comprises an elongated composite structure having a longitudinal axis, comprising a first member and second member, wherein the first member and second member are adjacent to each other and in communication such that the first member and second member together form a substantially circular cross-section, and wherein the composite structure defines a leading portion and a body portion. The term "substantially circular" cross-section, as used herein, includes oval or elliptical cross-sections. The leading portion may comprise a unitary tip and the body portion may comprise a rigid body, the body portion having a first section and a second section, the first section and the second section of the body portion being axially slidably movable relative to each other. Both the first section and the second section are connected to the unitary tip. The word "rigid" as used herein means rigid enough to allow axial movement through an endoscopic passageway without compromising structural integrity.

When the first section of the body portion retracts relative to the second section of the body portion and the second section of the body portion advances forward relative to the first section of the body portion, the leading portion is directed in a first direction at an angle relative to the a longitudinal axis of the elongated composite structure. When the first section of the body portion advances relative to the second section of the body portion, the leading portion is directed in a second direction, opposite to the first direction and at an angle relative to the longitudinal axis of the elongated composite structure.

In another embodiment, the invention is a steerable wire guide having a longitudinal axis, comprising a composite structure having a leading portion and a body portion, wherein the composite structure comprises a first member and a second member. The first and second members comprise interlocking components such that the first member is configured to be securely attached to the second member. The first member and second member are, however, axially movable relative to each other, such that concurrent movement of the first and second members in a first direction causes the first and second members to bend in unison in a first direction to advance the leading portion, while the concurrent movement of the first and second members in a second direction retracts the leading portion.

In yet another embodiment, the invention is a steerable wire guide comprising a composite structure having a longitudinal axis, comprising a substantially soft body portion and a substantially rigid body portion. The soft body portion has tapered configuration and the rigid body portion has an elongated configuration having a uniform diameter. The soft body portion is located at the distal end of the composite structure and the rigid portion located at the proximal end of the composite structure.

The composite structure also comprises a first interlocking portion and a second interlocking portion, wherein the first and second interlocking portions are concurrently axially movable relative to each other, such that the first and second portions slide relative to each other, and when the first portion of the composite structure advances, the relative movement of the each first and second interlocking portions directs the distal leading portion of the composite structure in a first direction at an angle relative to the longitudinal axis; but when the second portion of the composite structure advances, the leading portion at the distal end of the composite structure bends in a second direction at an angle relative to the longitudinal axis.

In still yet another embodiment, the invention is a steerable wire guide comprising an elongated composite structure, the composite structure comprising a first portion and a second portion, wherein the first portion is in communication with the second portion, and wherein the composite structure forms a leading portion having a tapered end including a flexible tip, and an elongated body portion having a uniform diameter.

The leading portion comprises a substantially soft material and the body portion comprises a substantially rigid material. The cross-section of the composite structure has a shape configuration, the shape configuration comprising a first member and a second member in communication with each other.

In still yet another embodiment, the wire guide comprises a first guiding wire section, a wire loop section and a second guiding wire section, the wire component being folded back on itself to form a generally central wire loop section; and a tubular sheath surrounding the first guiding wire section and the second guiding wire section.

The steerable wire guide can have a radiopaque marker on the composite structure. Independently, the steerable wire guide can have a covering positioned over at least a portion of the composite structure, particularly if needed to hold members of the wire guide adjacent to each other.

BRIEF DESCRIPTION OF THE DRAWINGS

These and other features and advantages of the present invention will be better understood by reference to the following detailed description when considered in conjunction with the accompanying drawings, wherein:

FIG. 1 is a side view of a steerable wire guide according to a first embodiment of the invention;

FIG. 2 is a top view of the steerable wire guide of FIG. 1, illustrating one embodiment of first and second members of the steerable wire guide, the cross-section of which is shown in FIG. 8;

FIG. 3 is a top view of the steerable wire guide of FIG. 1 in a first configuration, wherein the leading portion of the composite structure is directed in a first direction, and at an angle relative to the longitudinal axis of the elongated composite structure;

FIG. 6 is a top view of the steerable wire guide of FIG. 1 in an alternate configuration;

FIG. 7 is a top view of the steerable wire guide of FIG. 1 in an alternate configuration;

FIG. 20 is a cross-sectional view of a thirteenth embodiment of the steerable wire guide taken along line B-B of FIG. 2, and illustrating first, second and third members of the steerable wire guide;

FIG. 21 is a cross-sectional view of a fourteenth embodiment of the steerable wire guide taken along line B-B of FIG. 2, and illustrating two parallel lumens disposed within a larger lumen in the steerable wire guide;

FIG. 22 is an illustration of the steerable wire guide comprising a coating;

FIG. 23 an illustration of the steerable wire guide comprising a coating over a portion of the wire guide;

FIG. 24 is a top view of a releasable connector detachably connecting a gripping portion of a removable handle and a tubular member proximal end according to one embodiment of the invention;

FIG. 25 is a top view of a releasable connector detachably connecting a gripping portion of a removable handle and a tubular member proximal end according to an alternate embodiment of the invention;

FIG. 26 is a top view of a releasable connector detachably connecting a gripping portion of a removable handle and a tubular member proximal end according to a second alternate embodiment of the invention;

FIG. 27 is a top view of a releasable connector detachably connecting a gripping portion of a removable handle and a tubular member proximal end according to a third alternate embodiment of the invention;

FIG. 28 is a top view of the steerable wire guide of an alternate embodiment of the invention comprising a loop;

FIG. 29 is a cross-section of the embodiment of FIG. 28, taken along line 29-29 of FIG. 28;

FIG. 30 is a top view of the steerable wire guide of FIG. 28 illustrating the first and second members concurrently moving distally and leading portion advancing in the first direction; and FIG. 31 is a top view of the steerable wire guide of the alternate embodiment of the invention comprising a loop as shown in FIGS. 28 and 30, further illustrating a ground section of a wall of the loop.

DETAILED DESCRIPTION OF THE DRAWINGS AND PREFERRED EMBODIMENTS

Figure 4:
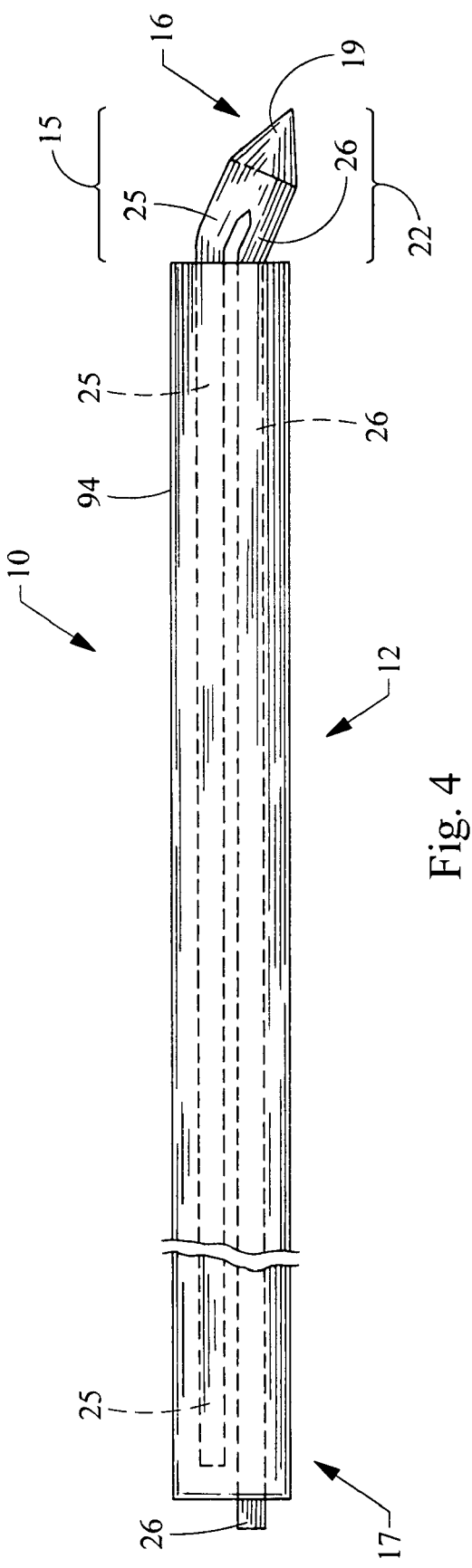
FIG. 4 is a top view of the steerable wire guide of FIG. 1 in a second configuration, wherein the leading portion of the composite structure is directed in a second direction, opposite the first direction, and at an angle relative to the longitudinal axis of the elongated composite structure.

Turning now to the figures, reference numbers are used to designate corresponding elements in the figures. Although the present invention has been described with reference to preferred embodiments, those skilled in the art will recognize that changes may be made in form and detail without departing from the spirit and scope of the invention. As such, it is intended that the following detailed description be regarded as illustrative rather than limiting and that it is the appended claims, including all equivalents thereof, which are intended to define the scope of the invention. The designations "top view" and "side view" are for orientation relative to each other only, as the device can be turned in any direction, which allows operation in any plane and access to virtually any structure.

The following paragraphs have been provided by way of general introduction, and are not intended to limit the scope of the following claims. The presently preferred embodiments, together with further advantages, will be best understood by reference to the following detailed description.

FIG. 1 illustrates a steerable wire guide 10 in accordance with the present invention. Steerable wire guide 10 enables the user to direct and steer wire guide 10 through a body lumen. Wire guide 10 may comprise a first member 25 (hidden from view in FIG. 1) and a second member 26 (such as first member 25a and a second member 26a shown in FIGS. 2 and 8, or other pairs of first and second members whose cross-sections are shown in FIGS. 9-20) interconnected to form an elongated composite structure 12. The first member 25 and the second member 26 are joined such that the cross section of the composite structure 12 is substantially circular. The diameter of the substantially circular cross section may vary as desired. To maneuver the composite structure 12, the first member 25 and the second member 26 slide relative to each other such that the advancement or extension of the first member 25 causes the second member 26 to retract. In the alternative, the retraction of the first member 25 causes the second member 26 to advance or extend, thereby allowing the user to control the direction in which the distal end 16 of the wire guide 10 extends. The first member 25 and the second member 26 can be connected together by a variety of methods known in the art.

The composite structure 12, which is formed when the first member 25 and the second member 26 are joined, can be turned in any direction, preferably within 180 degrees of the longitudinal axis 14 of the composite structure 12. The first member 25 and the second member 26 can also be oriented to slide in opposite directions such that the movement of the composite structure 12 can be turned 360 degrees.

As further shown in FIG. 1, the composite structure 12 has a leading portion 15 at the distal end 16 of wire guide 10 and a body portion 18 that includes the proximal end 17 of wire guide 10. The leading portion 15 may have a taper wherein the diameter of the leading portion 15 is less than the diameter of the body portion 18. When used with a catheter system, the leading portion 15 is inserted to correspond to the distal end of the catheter and the body portion 18 corresponds to the main body at the proximal region of the catheter. The body portion 18 can have a gradually increasing, gradually decreasing or uniform diameter. Preferably, the diameter of the body portion 18 should be sufficient to facilitate the transportation of medical devices over the composite structure 12 and may vary as desired.

The wire guide 10 has many advantages. The wire guide 10 can be maneuvered from the distal end 16 while the wire guide 10 is disposed within an internal body cavity. Consequently, delivery of medical devices or treatments to obstructed destination sites within a patient's body can be achieved. The wire guide 10 is flexible and can be used with or without the assistance of a catheter system. If the wire guide 10 is used with a catheter, the wire guide 10 can be used to manipulate the transport of the catheter or an alternative medical device through the patient's body cavities.

Figure 8:
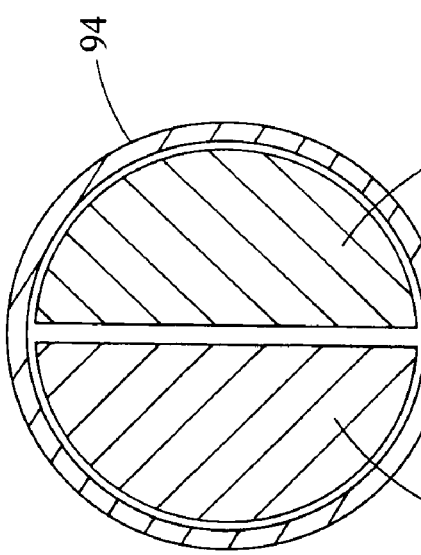
FIG. 8 is a cross-sectional view of one embodiment of the steerable wire guide taken along line A-A of FIG. 2, and illustrating first and second members of the steerable wire guide, as well as a unitary sheath surrounding them.

As shown in FIG. 3, the leading portion 15 of the wire guide 10 has a first configuration 20. In this embodiment, the first member 25 and the second member 26 are juxtaposed to form the composite structure 12. By way of non-limiting embodiments, the cross section of the composite structure 12 can be configured as shown in FIG. 8 or in alternate configurations as shown in FIGS. 9-20, discussed in greater detail below. The interconnecting relationship between first member 25 and the second member 26 can be self-locking or sealed by any conventional means, such as a covering positioned over at least a portion of the composite structure.

Any suitable material can be used for the composite structure 12, and a variety of suitable materials are known to those skilled in the art. The material chosen need only be biocompatible and able to be formed into the structures described herein. Examples of suitable materials include stainless steel, shape memory material such as Nitinol or other nickel-titanium alloys, MP35N® and other nickel-cobalt alloys, Cobalt L-605™ and other cobalt-chromium alloys, other biocompatible metals, metal-alloys, as well as polymeric materials.

The interior surface of the wire guide 10 can be a solid wire or made from a material similarly suitable for acute use in the human body. The composite structure 12 can be made of the same material uniformly or from multiple materials having different inherent property characteristics.

Preferably, the composite structure 12 comprises a tubular member forming a sheath 94 about first member 25 and second member 26. The composite structure 12 can also be formed from a series of layers, or as a coated core structure. For example, the composite structure 12 can comprise a shape memory material with a solid core in one embodiment or a shape memory material core with a polytetrafluoroethylene covering in another embodiment. Depending on the desired range of movement of the wire guide, the appropriate material can be selected and configured as needed.

As shown in FIGS. 3 and 4, respectively, the leading portion 15 of structure 12 has a first configuration 20 and a second configuration 22. It is contemplated that the leading portion 15 can have alternate configurations that permit advancement of the wire guide when deployed. The angle at which the leading portion 15 moves or bends is related to the material used and configuration of the first and second members 25, 26. The leading portion 15 as shown in FIG. 3 can be turned to be, for example, substantially perpendicular to the longitudinal axis 14 of composite structure 12. The body portion 18 is substantially parallel to, or co-linear with, the longitudinal axis 14 during movement of the leading portion 15 from a first configuration 20 to a second configuration 22. The leading portion 15, however, can include a flexible tip 19 configured to facilitate transport through the patient's body cavity. The movements of the leading portion 15 are directed at the proximal end 17 of the wire guide 10. The leading portion 15 is approximately about 5 and 10 centimeters in length. The tip 19 of the leading portion 15 is approximately about 7 millimeters. In the alternative, the leading portion 15 may comprise a flexible loop 92, as shown in FIGS. 28-31. An example of a wire guide with a loop tip that can be used in conjunction with the present invention is disclosed in the U.S. application Ser. No. 10/719,764, filed Nov. 21, 2003, and entitled "Loop Tip Wire Guide," now U.S. Pat. No. 7,520,881, which is incorporated herein by reference.

Figure 5:
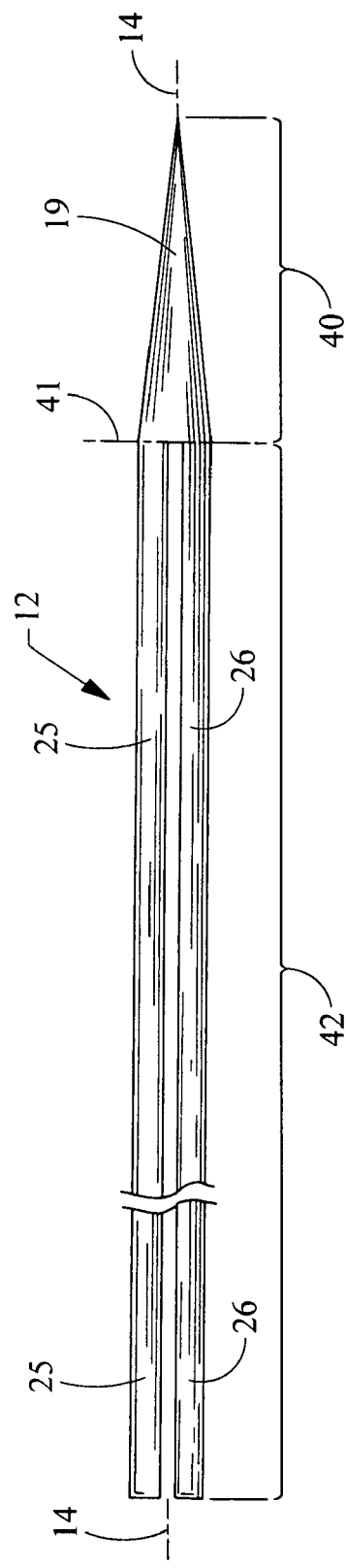
FIG. 5 is a top view of the steerable wire guide of FIG. 1, illustrating the first and second members of the steerable wire guide.

As shown in FIGS. 5-7, a junction 41 separates the soft body portion 40 and the rigid body portion 42. In this embodiment, members 25, 26 of the composite structure 12 can be maneuvered at the distal end 16 of the composite structure 12 which in turn moves the tip 19 in one direction at an angle C (see FIG. 6) or in an opposite direction at an angle D (see FIG. 7) relative to the longitudinal axis 14. The body portion 42 is composed of a rigid material and the leading portion 40 is composed of a soft material, together forming the composite structure 12 of the steerable wire guide. In some embodiments, the rigid body portion 42 comprises a female section and a male section. The soft body portion 40 is a unitary structure. The soft body portion 40 can be maneuvered by sliding the first and second sections 25, 26 of the rigid body portion relative to each other, while the overall position of the rigid body portion does not change.

The first and second members 25, 26 can be enclosed in a unitary sheath 94 (as shown in FIG. 1). The first and second members 25, 26 can be joined at the distal end 16 of wire guide 10, to allow for the movement of either member in a first or second direction.

Consequently, the first member 25 is turned and maneuvered forward, causing deflection of the wire guide 10. The joining techniques of the first and second members 25, 26 vary depending on the materials used.

In an alternate configuration illustrated in FIGS. 28-31, including a flexible loop 92 at the distal end 16, the wire guide is elongated and subsequently bent to form the loop. The thickness the wall 44 of the loop 92 should be sufficiently narrow to provide flexibility in either the lateral or longitudinal direction. The first and second members 25, 26 can slide in the lateral direction relative to each other maintaining a constant diameter through the wire guide. The thickness of the wall 44 of the loop 92 can be made smaller in one portion (for example, to help the loop collapse to fit into a catheter) by grinding down the wall in a desired section 93, as shown in FIG. 31.

Alternate materials can be used. In one embodiment where a super elastic alloy is used, coil spring comprising platinum which can be easily viewed by x-ray, can be used for the loop or the elongated body or both. In yet other alternate embodiments, the cross section configuration of the loop and the first and second members can be any one of rectangular, flat, triangular, trapezoidal, pentagonal or hexagonal. This is not exhaustive or all-inclusive. The wire guide 10 can be, for example, four-sided (see FIG. 17), six-sided (see FIG. 18) or eight-sided (see FIG. 19) to provide sufficient flexibility to the desired user.

Alternative configurations of the first and second members are illustrated in FIGS. 8-20. In these figures, a variety of different cross-sectional configurations are shown. Some of the configurations feature interlocking female and male members. FIGS. 8-20 are intended to be non-limiting embodiments of the invention and are used solely for providing a further understanding of the invention.

For example in FIG. 8, the first member 25a and the second member 26a are shaped as congruent halves. The combined cross section of first member 25a and second member 26a is substantially circular. The first member 25a and second member 26a are equally proportioned in size and shape. It is contemplated that the first member 25a and second member 26a can have a solid core, as shown in FIG. 8; or that either the first member or the second member, or both, can have a hollow core.

Figure 9:
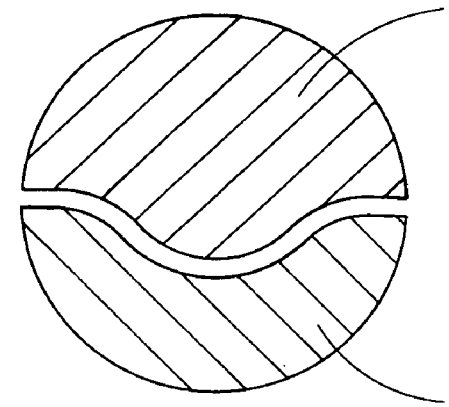
FIG. 9 is a cross-sectional view of a second embodiment of the steerable wire guide taken along line B-B of FIG. 2, and illustrating first and second members of the steerable wire guide.

In FIG. 9, an alternate shape for the first member 25 and second member 26 are shown as first member 25b and second member 26b, respectively.

In FIGS. 11, 12, 14, 15, and 16, the first members 25d, 25e, 25g, 25h and 25i; and the second members 26d, 26e, 26g, 26h and 26i, respectively, are interconnected to form elongated composite structures. The combined cross section of the first member 25 and second member 26 is in each case substantially circular. The first member 25 and the second member 26 can be joined using various methods known in the art such that the first member 25 and second member 26 can be separated as needed. A coating (or covering) can be applied about the circumference of the first member 25 and second member 26 such that the union forms a composite structure.

Figure 10:
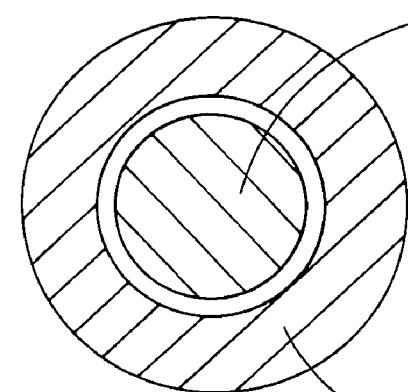
FIG. 10 is a cross-sectional view of a third embodiment of the steerable wire guide taken along line B-B of FIG. 2, and illustrating first and second members of the steerable wire guide.

In FIG. 10, the first member 25c is concentrically disposed around second member 26c. The first member 25c and the second member 26c are in communication with each other and can be assembled by inserting the second member 26c into the first member 25c.

Figure 11:
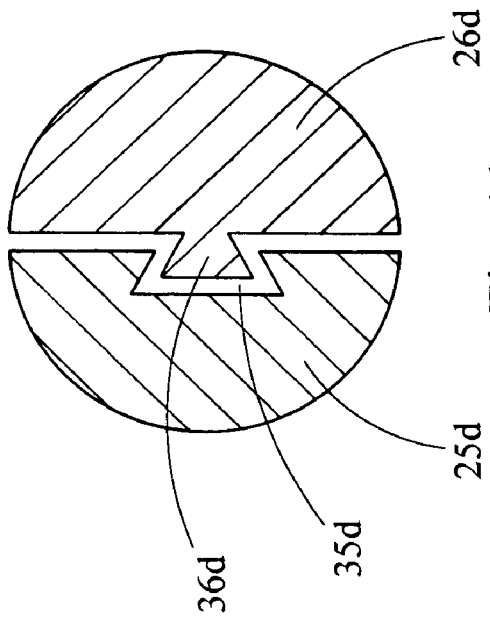
FIG. 11 is a cross-sectional view of a fourth embodiment of the steerable wire guide taken along line B-B of FIG. 2, and illustrating first and second members of the steerable wire guide.

In FIG. 11, the first member 25d has a channel 35d that extends the length of the composite structure. The second member 26d has a protruding portion 36d that extends the length of the second member 26d. The protruding portion 36d of second member 26d is inserted into the channel 35d of first member 25d, forming an elongated composite structure. Alternatively, both first member 25d and second member 26d can have both a channel and a protruding portion side-by-side, so that the protruding portion of each is disposed in the channel of the other.

Figure 12:
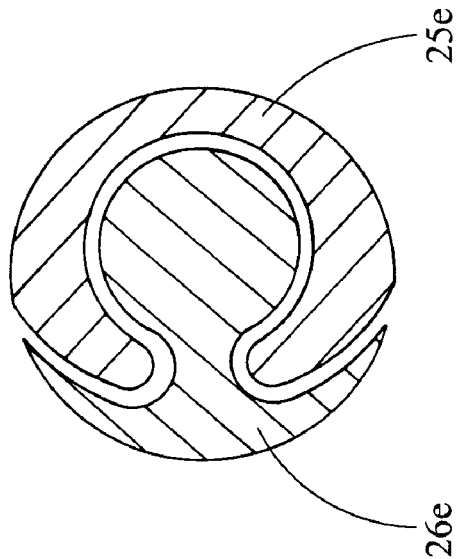
FIG. 12 is a cross-sectional view of a fifth embodiment of the steerable wire guide taken along line B-B of FIG. 2, and illustrating first and second members of the steerable wire guide.

In FIG. 12, the first/female member 25e has an "U-shaped" configuration. The second/male member 26e is inserted into the first member 25e, forming a substantially circular cross section.

Figure 13:
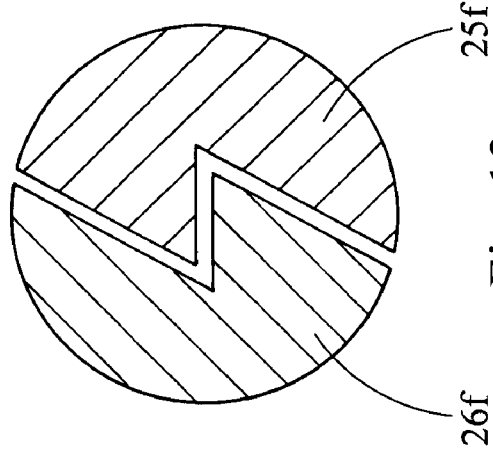
FIG. 13 is a cross-sectional view of a sixth embodiment of the steerable wire guide taken along line B-B of FIG. 2, and illustrating first and second members of the steerable wire guide.

In FIG. 13, the first member 25f has a first "zig-zag" configuration and the second member 26f has a complementary "zig-zag" configuration. The first member 25f and second member 26f are interconnected such that the first and second members 25f, 26f together form a substantially circular cross section. The first member 25f and the second member 26f can be joined together using any method known in the art such that the first member 25f and the second member 26f form a composite structure that can be separated manually, using a mechanical device or a combination thereof.

Figure 14:
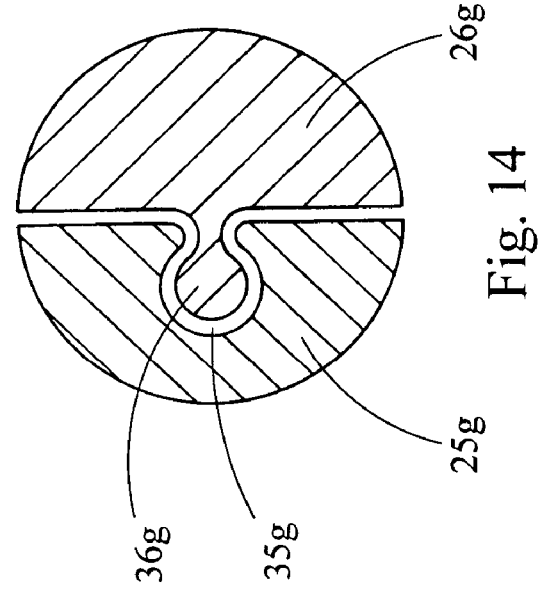
FIG. 14 is a cross-sectional view of a seventh embodiment of the steerable wire guide taken along line B-B of FIG. 2, and illustrating first and second members of the steerable wire guide.

In FIG. 14, the first/female member 25g has a recessed portion 35g and the second/male member 26g has a protruding portion 36g, such that the protruding portion 36g is substantially disposed within the recessed portion 35g.

Figure 15:
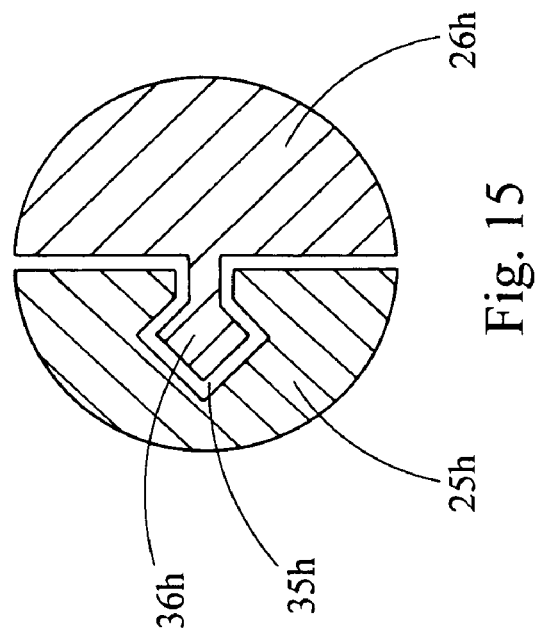
FIG. 15 is a cross-sectional view of a eighth embodiment of the steerable wire guide taken along line B-B of FIG. 2, and illustrating first and second members of the steerable wire guide.

In FIG. 15, the first/female member 25h has a recessed portion 35h having an alternate configuration, and the second member 26h has a protruding portion 36h such that first member 25h and the second member 26h together form a substantially circular cross section and elongated tubular body.

Figure 16:
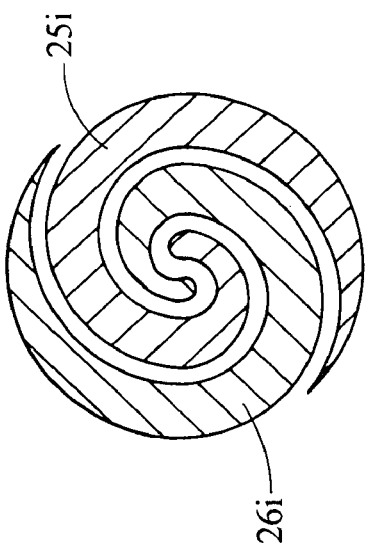
FIG. 16 is a cross-sectional view of a ninth embodiment of the steerable wire guide taken along line B-B of FIG. 2, and illustrating first and second members of the steerable wire guide.

In FIG. 16, the first member 25i has a first concentric configuration and the second member 26i has a second concentric configuration, wherein the first configuration is in communication with the second configuration. In this embodiment, the first member 25i and second member 26i form a substantially elongated tubular structure.

In one embodiment (not shown), the steerable wire guide can be used to cannulate a duct. If the steerable wire guide is intended to cannulate the common bile duct, the suitable dimensions for the combined diameter of the first and second members can be about a range of 0.4 millimeters and 1 millimeter, and preferably, a diameter about 0.5 and 0.9 millimeters.

Figure 17:
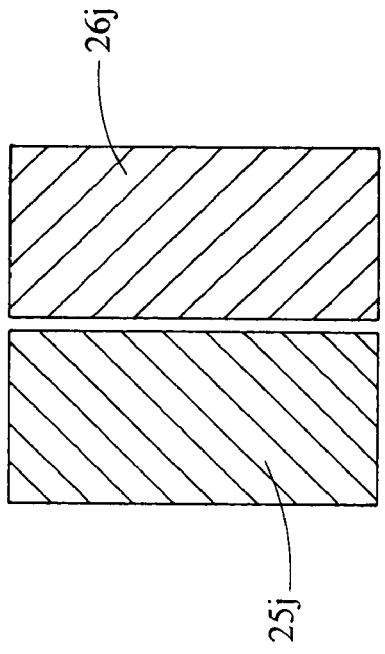
FIG. 17 is a cross-sectional view of a tenth embodiment of the steerable wire guide taken along line B-B of FIG. 2, and illustrating first and second members of the steerable wire guide.

In FIG. 17, the cross-sectional shape configuration has four sides. In this embodiment, the wire guide 10 is comprised of a first member 25j and a second member 26j which each have a smaller four sided shape configuration.

Figure 18:
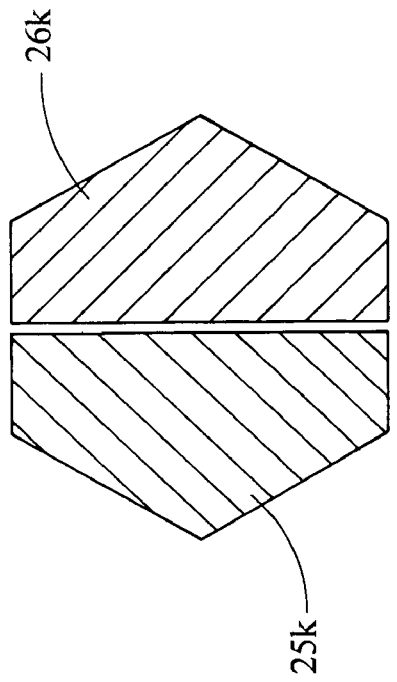
FIG. 18 is a cross-sectional view of a eleventh embodiment of the steerable wire guide taken along line B-B of FIG. 2, and illustrating first and second members of the steerable wire guide.

In FIG. 18, the pentagonal cross sections of the first member 25k and the second member 26k together form a hexagon.

Figure 19:
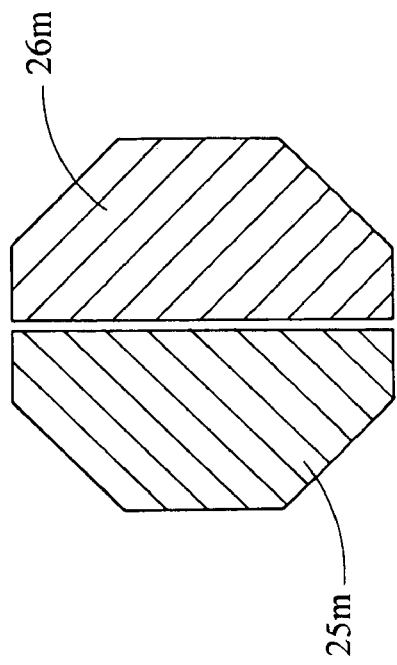
FIG. 19 is a cross-sectional view of a twelfth embodiment of the steerable wire guide taken along line B-B of FIG. 2, and illustrating first and second members of the steerable wire guide.

In FIG. 19, the hexagonal cross sections of the first member 25m and the second member 26m together form an octagon. In the configurations of FIGS. 18 and 19, the cross section of the first and second members provides for the ability to have a larger diameter and a reinforced structural shape for withstanding compression forces in the body vessel.

FIG. 20 illustrates a cross section comprising tri-part members 31, 32 and 33. The tri-part members can be equal shape and size or have varying configurations, such that in either case the total circumference formed is substantially circular.

In FIG. 21, there are two parallel lumens 37, 38 disposed within a larger lumen 39. In this configuration, multiple lumens are provided to accommodate multiple access points disposed through the wire guide.

The structures of the first member 25 and the second member 26 can be formed by various techniques, depending on their shape. Complex shapes are best formed by extrusion. Flat surfaces can be cut, for example with a laser.

The first member 25 and the second member 26 can be joined together at the distal end by various techniques, for example by crimping, welding, soldering, or gluing. Some materials (e.g. nylon) can be fused together by the application of heat. If a molded loop is used, the loop may be overmolded or heat shrunk on the first and second members to join them together.

The steerable wire guide 10 can be used in conjunction with a catheter. The catheter can include a lumen extending therethrough whereby the steerable wire guide 10 can be inserted. Upon insertion, the steerable wire guide 10 can be controlled from the distal end 16 of the wire guide in the distal end of the catheter to maneuver the catheter in the patient's body cavity. An example of a catheter system that can be used in conjunction with the present invention is disclosed in the U.S. application Ser. No. 11/269,991, filed Nov. 9, 2005, and now abandoned, which claims priority to U.S. Provisional Application Ser. No. 60/626,694, filed Nov. 9, 2004, entitled "Steerable Catheter," which is incorporated herein by reference. The diameter of the steerable wire guide 10 can be significantly less than the diameter of the inner lumen of the catheter body. Despite the small diameter, the steerable wire guide 10 is well suited for injecting therapeutics or contrast agents or other treatments prescribed by a physician. The steerable wire guide 10 has sufficient torsional stability to facilitate steering of the steerable wire guide 10 within the lumen of the catheter.

Optionally, the steerable wire guide 10 can comprise a coating 60 as shown in FIG. 22. Coating 60 can be positioned over the entire composite structure or just a portion thereof. Specifically, FIG. 23 shows a partial coating of the composite structure 12 as well as the leading portion 15. The coating 60 can be applied to retain the first and second members 25, 26.

The coating 60 can be positioned over a portion of, or the entire, composite structure 12, including loop 92 (see FIGS. 28-31).

The coating 60 can be polytetrafluoroethylene ("PTFE"), or another suitable material. Examples of suitable coverings include fluoropolymers, polyurethanes, and other suitable coatings used in the medical device arts. The coating 60 may be applied by dipping, molding, or spraying a suitable coating material, such as polytetrafluoroethylene, urethane, and/or other polymeric coatings directly to the desired portions of the steerable wire guide. Alternatively, the coating may be applied by heat shrinking a heat shrinkable material about the desired portions of the steerable wire guide.

One preferred coating comprises a thin PTFE heat shrinkable material. The heat shrinkable nature of these materials facilitates manufacturing while providing a lubricious coating, which facilitates navigation. In preferred embodiments, the thickness of the coating is between approximately 2.5 micrometers and 2.5 millimeters. In some embodiments, the thickness of the coating is between approximately 2.5 micrometers and 100 micrometers. In other embodiments, the thickness of the coating can be between approximately 2.5 micrometers and 50 micrometers. These preferred thicknesses provide suitable coatings while not adding significantly to the overall thickness of the device.

Radiopaque materials known in the art including, but not limited to, bismuth or gold can be added in the coating 60. Also, radiopaque markers known in the art can be placed on the composite structure 12. Several examples of suitable radiopaque materials and markers are known in the art, and any suitable material and/or marker can be utilized in the present invention.

The steerable wire guide 10, with or without coating 60, may be treated with a hydrophilic coating or hybrid polymer mixture, such as those based on polyvinyl pyrolidine in organic solvent solutions. These solutions make the wire guide particularly lubricious when in contact with body fluids, which aids in navigation.

A means for operating the steerable wire guide 10 such as a handle 90 can be attached at the proximal end. The handle 90 allows the operator the ability to control the movement of the first and second members 25, 26 while simultaneously providing a structure to hold the steerable wire guide 10. The handle 90 can vary as needed and suitable configurations known in the art can be used. Optimally, the handle 90 includes a lumen extending therethrough wherein a wire can be disposed through each member and terminate at the proximal end 17.

Optionally, as shown in FIGS. 24-27, the handle 90 can be removable, detachably connected to the proximal end 17. The handle 90 facilitates the user's ability to manipulate the first and second members 25, 26. The handle 90 further provides the user with the option of retracting the composite structure 12 from the patient, thereby permitting the exchange of other medical devices over the composite structure 12. Alternatively, the user is provided with the option of retracting the composite structure 12 from the patient, thereby permitting the exchange of other wire guides through the wire guide 10.

The handle 90 comprises a gripping portion 84 and a releasable connector 82 that detachably interconnects the gripping portion 84 and the proximal end 17. Several embodiments of releasable connector 82 are contemplated, including, but not limited to, an interference fit (see FIGS. 24 and 25), a threaded connection (see FIG. 26) and a snap-fit connection (see FIG. 27). For example, FIGS. 24 and 25 illustrate exemplary embodiments of a releasable connector 82 forming an interference fit connection with the proximal end 17. In the embodiment shown in FIG. 24, the releasable connector 82 comprises a longitudinal bore 96 with which the proximal end 17 forms an interference fit. Alternatively, in the embodiment shown in FIG. 25, the releasable connector 82 comprises a protrusion 80 defining an interior lumen through which the proximal portions of the first and second members 25, 26 extend. Protrusion 80 forms an interference fit at proximal end 17 of the composite structure 12.

FIG. 26 illustrates a releasable connector 82 having an internal longitudinal bore 96 having internal threads 97 which engage external threads 98 on the proximal end 17 of the composite structure 12.

Alternatively, but not shown, the releasable connector comprises a protrusion having external threads and the proximal end comprises an expanded portion having internal threads. Thus, the removable handle is releasably attached to the proximal end by threading the protrusion of the releasable connector into the expanded portion of the proximal end of the wire guide.

FIG. 27 illustrates a non-limiting exemplary embodiment of a releasable connector 82 that forms a snap-fit connection with the proximal end 17. In this embodiment, the releasable connector 82 comprises a longitudinal bore 96 having an internal recess 100 and the proximal end 17 is received therein. The proximal end 17 comprises a ridge 102 that snaps into the internal recess 100 of the longitudinal bore 96.

In any of the configurations shown in FIGS. 24-27, the first and second members 25 and 26 can be connected to control buttons 104 and 106, respectively, which can be moved forward or backward relative to handle 90, to advance or retract the member to which it is attached.

As shown in FIGS. 28-31, the steerable wire guide 110 can comprise an elongate member 112 having a longitudinal axis 114, a leading portion 115 and a body portion 118, the elongate member 112 further comprising a wire component 125, 92, 126 comprising a first guiding wire section 125, a wire loop section 92 and a second guiding wire section 126, the wire component being folded back on itself to form the wire loop section 92 in a generally central part of the wire component, and a tubular sheath 94 surrounding the first guiding wire section 125 and the second guiding wire section 126 to form the body portion 118 of the elongate member 112, and the wire loop section 92 of the wire component constituting the leading portion 115 of the elongate member 112; the first 125 and second 126 guiding wire sections being movable relative to each other and with respect to the tubular sheath 94 such that: relative distal movement of the first guiding wire section 125 with respect to the second guiding wire section 126 directs the leading portion 115 in a first direction 121 at an angle relative to the longitudinal axis 114, relative distal movement of the second guiding wire section 126 with respect to the first guiding wire section 125 directs the leading portion 115 in a second direction 122 different from the first direction 121, concurrent distal movement of the first 125 and second 126 guiding wire sections moves the leading portion 115 in a third direction 123, and concurrent proximal movement of the first 125 and second 126 guiding wire sections moves the leading portion 115 in a fourth direction 124 opposite to the third direction 123; wherein the first direction 121 is away from a first side of the longitudinal axis 114 and the second direction 122 is away from a second side of the longitudinal axis 114, the first side generally being opposite the second side. Optionally, the steerable wire guide can further comprise a closure member 54 closing the wire loop section 92, as shown in FIG. 30. Independently, a part of the wire loop section 92 can be ground smaller in one portion 93 of the wall 44 of the wire loop section 92, as shown in FIG. 31. If the wire used is 0.030 inches or 0.75 mm in diameter, for example, the wire can be ground to a thickness as small as 0.010 inches or 0.25 mm, in order to control the stiffness (and hence the loop size) of the wire loop section 92. Alternatively, the wire need not be ground at all, if it is already of the desired stiffness to form the desired loop size.

The wire loop section 92 is preferably formed, for example, as shown in FIG. 30, at about the mid-portion of the wire component. In these embodiments, the wire component is bent at about its mid-portion to form the wire loop section 92 of the leading portion 115.

As an alternative to forming a wire loop section from the wire component, a separate member defining a loop can be affixed to two substantially straight wires to form the steerable wire guide of the present invention (not shown). This may be advantageous when it is desirable to form the loop and elongate member of different materials. For example, a nylon or silicone loop can be formed and attached, such as by a closure member, to an elongate member formed of Nitinol™.

Steerable wire guides 10 or 110 may be formed with or without closure member 54. The closure member 54 can close the loop or wire loop section 92 such that no opening exists to the interior space of the loop or wire loop section 92. Any suitable closure member can be used, including bonds, adhesives, and separate members. Examples of suitable closure members include sutures or other appropriate material tying the two sections together, adhesive bonds and other bonds (such as a solder bond, a welded bond, or a molded bond) and a connector (such as a rivet). The closure member 54 can be tightened, such as by crimping, to fix the loop or wire loop section 92 in overall size. In an alternate embodiment, not shown, the closure member 54 can be a molded bond. The loop or wire loop section 92 can be formed by molding two sections of the elongate member together. In another alternate embodiment, the closure member 54 is a welded bond. Two sections of the composite member 12 can be welded or soldered together to form loop or wire loop section 92.

More specifically, the loop can be formed from two sections of the composite structure wound about each other. In yet another alternate embodiment (not shown), the closure member is integral with the composite member. In this case, the loop and the composite structure of the steerable wire guide are formed using laser cutting techniques as are known to those skilled in the art. The closure member 54 can be formed of any suitable material, and need only be biocompatible and capable of maintaining the loop or wire loop section 92 in a closed position. Preferably, the closure member 54 comprises a cannula formed of stainless steel or a shape memory material, such as Nitinol™. Also preferable, the closure member 54 is able to maintain a tightened position on the composite structure 12 upon application of a suitable force, such as by applying a crimping workload to the closure member 54.

The proximal end 17 may alternatively include a molded loop 92 to facilitate the steerable wire guide entry into catheters or other similar devices. The thickness of a wall 44 of molded loop 92 can be about 0.014 inches and the width 52 of molded loop 92 can be about 0.075 inches. The length 50 of the molded loop 92 can vary as desired but preferably be about 0.150 inches. The molded loop 92 can be configured in alternate configurations as need. The preferred material of the molded loop is a plastic with a radiopaque coating, or a shape memory material. This is not an exhaustive material list. Further included in this configuration is a composite structure 12. The composite structure 12 can be comprised of a single or multiple wire configurations. The diameter of collapsed molded loop 92 should be approximately equally to the diameter of the composite structure 12.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction were believed to be well within the ability of one rudimentary skilled in the area in view of the present disclosure. Illustrative embodiments of the present invention have been described in considerable detail for the purpose of disclosing a practical, operative structure whereby the invention may be practiced advantageously. The designs described herein are intended to be exemplary only.

It is therefore intended that the foregoing detailed description be as illustrative rather than limiting, and that it is the following claims, including all equivalents, that are intended to define the spirit and scope of this invention.

What is claimed is:

1. A steerable wire guide having a longitudinal axis, comprising:
   a composite structure comprising
      a first member and a second member which are joined together by a flexible loop at the distal end of a leading portion at the distal end of the composite structure,
      a tubular sheath surrounding the first member and the second member, and
      a handle at the proximal end of the tubular sheath, connected to the first and second members, to control movement of the first and second members;
   wherein the first member and second member are movable relative to each other and relative to the tubular sheath such that concurrent movement of the first and second members in a first direction causes the first and second members to advance the leading portion, while the concurrent movement of the first and second members in a second direction retracts the leading portion; and such that movement of the first member relative to the second member in a first direction moves the leading portion in a third direction, and movement of the first member relative to the second member in a second direction opposite the first direction, moves the leading portion in a fourth direction, opposite the third direction, and
   wherein the first member is concentrically disposed around the second member.

2. The steerable wire guide of claim 1, wherein the cross sections of the first and second members are substantially circular.

3. The steerable wire guide of claim 1, wherein the loop is plastic.

4. The steerable wire guide of claim 1, wherein the loop is plastic with a radiopaque coating.

5. The steerable wire guide of claim 1, wherein the loop is a shape memory material.

* * * * *